United States Patent [19]

Peplinski

[11] Patent Number: 5,426,509
[45] Date of Patent: Jun. 20, 1995

[54] DEVICE AND METHOD FOR DETECTING FOREIGN MATERIAL ON A MOVING PRINTED FILM WEB

[76] Inventor: Robert A. Peplinski, 9200 Seneca N.W., Massillon, Ohio 44646

[21] Appl. No.: 64,420

[22] Filed: May 20, 1993

[51] Int. Cl.⁶ ............................................. G01N 21/89
[52] U.S. Cl. .................................... 356/430; 250/572; 356/402
[58] Field of Search ................ 356/237, 239, 430, 431, 356/402; 250/572

[56] References Cited

U.S. PATENT DOCUMENTS

| | | | |
|---|---|---|---|
| 3,479,518 | 11/1969 | Akamatsu et al. | 356/430 X |
| 3,480,786 | 11/1969 | Kottman | 356/431 X |
| 4,160,601 | 7/1979 | Jacobs | 356/404 |
| 4,320,967 | 3/1982 | Edgar | 356/51 |
| 4,538,912 | 9/1985 | Shaw | 356/366 |
| 4,550,433 | 10/1985 | Takahashi | 382/7 |
| 4,556,903 | 12/1985 | Blitchington | 358/106 |
| 4,739,176 | 4/1988 | Allen et al. | 356/430 X |
| 4,861,164 | 8/1989 | West | 356/445 |
| 4,898,471 | 2/1990 | Stomestrom | 356/394 |
| 4,976,540 | 12/1990 | Kitamura | 356/38 |
| 4,991,970 | 2/1991 | Darboux et al. | 356/402 |
| 4,992,949 | 2/1991 | Arden | 356/237 |
| 5,062,707 | 11/1991 | Adler-Golden | 356/311 |
| 5,072,128 | 12/1991 | Hayano | 356/237 |

FOREIGN PATENT DOCUMENTS 60-97245  5/1985  Japan ..................... 356/237

Primary Examiner—Vincent P. McGraw
Attorney, Agent, or Firm—Oldham, Oldham, & Wilson Co.

[57] ABSTRACT

A device for detecting contaminant particles on a surface of a monochrome web of material of a first color imprinted with a second color different from said first color comprises a frame member with a feed roll of said web material and a takeup roll, with the web material passing from said feed roll to said takeup roll past an inspection stage between the feed roll and takeup roll. The inspection stage has a light detecting means mounted on it for collecting light transversely from the web as the web moves past the inspection stage. The light detecting means is communicated to a light analyzing means to observe variations in the collected light and the light analyzing means is communicated to a means for indicating that a variation beyond a threshold amount has been observed by the light analyzing means. In preferred embodiment, the light collected by the light detecting device is passed through a filter immediately prior to collection in said light detection device, said filter selected so that said first color is indistinguishable from said second color after passage through the filter.

13 Claims, 1 Drawing Sheet

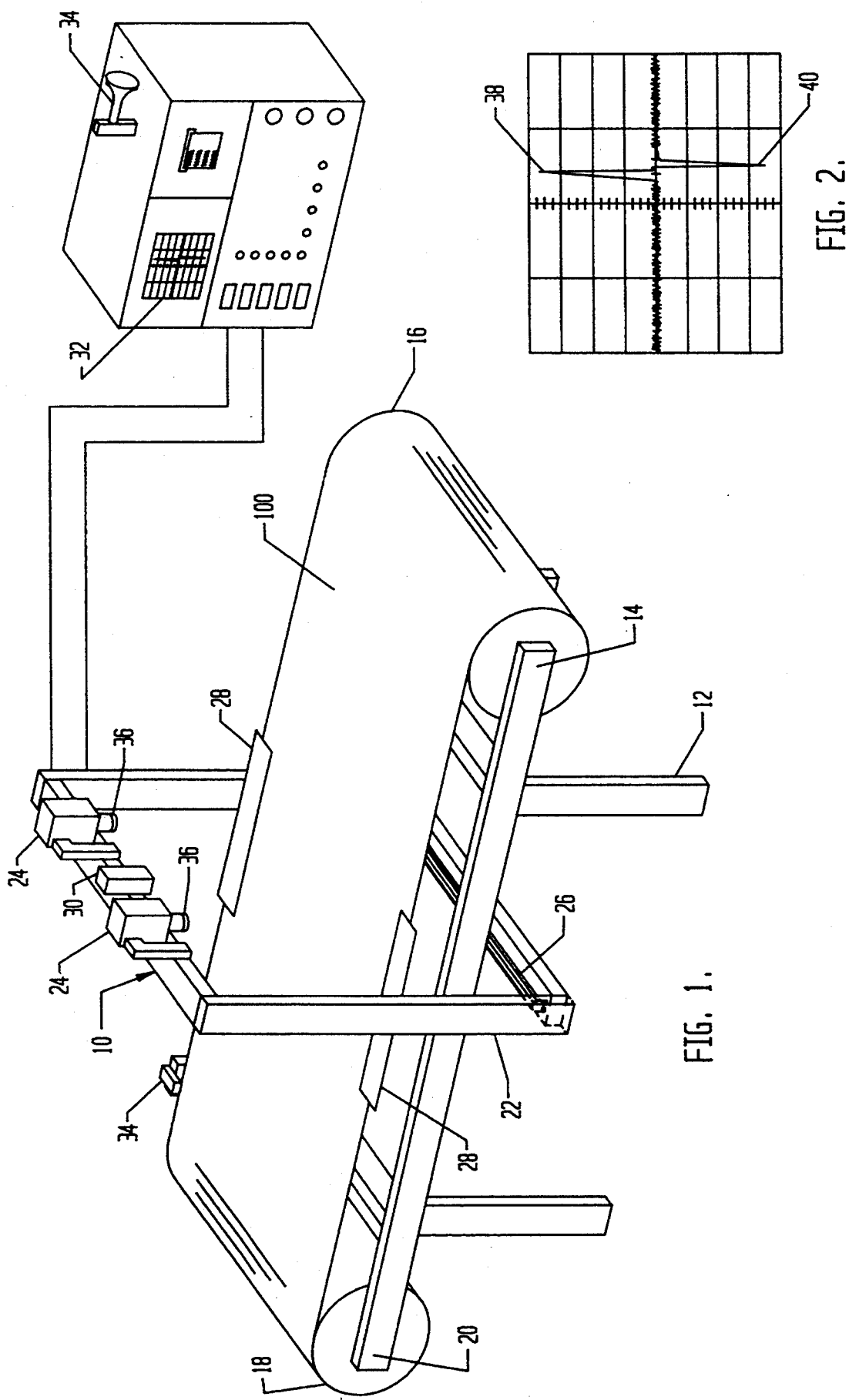

DEVICE AND METHOD FOR DETECTING FOREIGN MATERIAL ON A MOVING PRINTED FILM WEB

The present invention relates to a device and method for detecting the presence of contaminant particles on or within a moving web of material. More particularly, the present invention relates to a device and method for detecting such particles on a printed web where the web is a first color and the imprinting thereupon is a second color. The device and method are applicable to both single film webs and laminated film webs, although the most important applications may be with laminated film webs.

BACKGROUND ART

Imprinting webs of material is an old art that has undergone major changes in the last century. One of the disadvantages of the high speed with which the webs are imprinted is the difficulty or sheer inability to manually inspect the surface or surfaces of such webs for contaminants. This inability to inspect can result in unacceptably high customer returns. These problems can be especially pronounced in the food and medical packaging industries.

One alternative is to provide an automated inspection system that can scan the surfaces, looking for the contaminants either on the surface, or within the surface, in the case of a laminated film web. The particular contaminants that are of concern are carbon particles, poly gels, insects or insect parts, dirt or other matter. The desired sensitivity of contaminant detection would be in the range of 0.4 square millimeters on a web of up to 48 inches wide moving at speeds of up to 1000 feet per minute.

Single film webs usually do not present much problem for scanning for contaminants, since they are easily scanned prior to printing. However, the device of the present invention provides capability of scanning after lamination and printing of laminated films, particularly where the contaminant can be captured between the film layers during the imprinting or laminating process.

SUMMARY OF THE INVENTION

An object of the invention is to provide a device that can scan the surface of a single color web of material imprinted with a second single color and to detect the presence of contaminant particles thereon without considering the imprinting to be a contaminant.

This and other objects of the invention are achieved by a device for detecting contaminant particles on a surface of a monochrome web of material of a first color having monochrome printing of a second color different from said first color. Such a device comprises a frame member with an intermediate portion, a light source, a light detecting means, a light analyzing means, and an indicating means. The frame member is provided with a means for mounting a feed roll of the web material and a means for mounting a takeup roll, the web material passing from the feed roll to the takeup roll. The intermediate portion of the frame member is between the feed roll and the takeup roll, and has a light detecting means mounted thereupon for collecting light transversely from the web as the web passes past it. The light source is mounted so as to direct a light beam upon a surface of the web. The light analyzing means determines when variation beyond a threshold amount has been observed by the light detecting means, and is communicated to the light analyzing means. The indicating means is to notify a human operator that a variation beyond a threshold amount has been observed by the light detecting means and determined by the light analyzing means, and the indicating means is communicated to the light analyzing means. The indicating means could be an audio alarm, an ink jet to mark upon the web, an automatic brake to stop the movement of the web, or other means as might be known in the web printing industry.

In the device, the light collected by the light detection device is passed through a filter immediately prior to collection in the light detection device. This filter is selected so that the first color is indistinguishable from the second color after passage through said filter. In other words, the filter effectively masks any markings of the second color on the web.

In one embodiment, the intermediate portion has a light controlling means mounted thereon proximate to the light detecting means and communicated to the light source, to control the amount of light emitted from said light source.

In one embodiment, the light source is located on the same side of the web as the light detecting means and the light detected is reflected off of a first surface of said web. In another embodiment, the light source is located on the opposite side of the web from the light detecting means and the light detected is passed through the web.

The invention also comprises a method for detecting contaminant particles on a surface of a monochrome web of material of a first color and imprinted with a second color different from the first color. This method comprising the steps of:

(a) passing the monochrome web from a feed roll to a takeup roll on a detection device, the web moving past an intermediate portion of the detection device between said feed roll and said takeup roll;

(b) collecting light from a light source in a light detecting means by transversely scanning the surface of said web with a light detection device as the web moves past the intermediate portion;

(c) analyzing for variations in the intensity of said collected light; and (d) causing observed variations in the collected light intensity beyond a threshold amount to trigger an indicating means, notifying a human operator of the detected variation.

In one embodiment of the method, the monochrome web is transparent or translucent and the light collected in step (b) is passed through the web. In another embodiment, the monochrome web is opaque and the light collected in step (b) is reflected off of the imprinted surface of the web.

The indicating means used could be an audio alarm, an ink jet to mark the web, an automatic brake to stop the movement of the web, or other indicating means known to one of skill in this art.

In one embodiment of the invention, the light collected in step (b) is passed through a filter immediately prior to collection in said light detection device, said filter selected so that said first color is indistinguishable from said second color after passage through said filter.

BRIEF DESCRIPTION OF THE DRAWINGS

Other objects and advantages of the present invention will be apparent from the following description taken in conjunction with the accompanying drawings, wherein identical parts are referred to with identical part numbers and wherein:

FIG. 1 shows a perspective view of the device of the present invention; and

FIG. 2 shows a typical oscilloscope output display illustrating the detection of contaminants on the web.

DETAILED DESCRIPTION OF THE DRAWINGS

The preferred embodiment device of the present invention may be best understood when reference is had to the Figures that are appended hereto. The device 10 comprises a frame member 12 with a means 14 for mounting a feed roll 16 of the web material 100 to be inspected, as the web material moves from the feed roll to a takeup roll 18, the takeup roll also preferably mounted to the frame member by a mounting means 20. Although not specifically illustrated in the Figures, it would be well known to one of skill in the art to have a drive mechanism attached to the means 20 for mounting the takeup roll 18 so that the web material 100 is pulled off of the freely-turning feed roll 16. Other aspects of the means for mounting would also be well known to those persons of skill in the handling of material webs on rolls, such as brakes, etc., so these aspects are not covered in detail, nor are they considered to be a part of the inventive concept taught hereby. Although the frame member 12 may be a stand-alone unit, it may also incorporate slitting knives or other appropriate roll processing tools, such as a laminator (none of which are illustrated), so that other processes may be accomplished simultaneously while the feed roll 16 of web material 100 is unwound.

An important aspect of the inventive concept is an intermediate portion 22 between the feed roll 16 and the takeup roll 18, the intermediate portion effectively serving as an inspection stage or theater. In order to act as an inspection stage, this intermediate portion 22 has at least one light detecting means 24 mounted on it for collecting light transversely across the web 100 as the web 100 passes the inspection stage. Typically, the light detecting means 24 will be provided by a video camera, particularly a solid state charge-coupled device (CCD) camera such as Part No. 3700-0001 and associated components, including a 60 mm lens, such as is commercially available from FlowVision Inc, a subsidiary of Kevlin Microwave Corporation, of Boston, Mass. Due to width of the web 100 as well as other factors, it may be preferred to provide two or more such cameras 24 to cover the entire transverse span of the web.

The light that is collected need not necessarily be provided by at least one light source 26 attached directly to the frame member 12, but it would be common practice to associate the light source with the frame member, since the intensity of the light drops off with the square of the distance from the source. A particular light source 26 that may be preferred is a tube-style fluorescent light, because such a light source can provide a uniform intensity across the web 100 if the fluorescent tube is positioned so its length runs transversely across the web. In the case of an optically clear web material, the light source 26 will be positioned on a first side of the web 100 and the light detecting means 24 on a second side, so light emanating from the light source must pass through the web in order to be detected. This will require that the edges of the web 100 be masked by an opaque material 28 so that no light can go around the web to reach the light detecting means 24. In the case of an opaque or otherwise not optically clear web, the light source 26 must be located on the same side of the web 100 as the light detecting means 24, in which case some shielding may be necessary to assure that the light reaching the light detecting means has reflected off of that web surface. Certainly, in this latter case of an optically non-clear web, the simultaneous detection of contaminants on both faces of the web 100 will require independent analysis means on each side of the web, as a single detection system is necessarily limited to inspecting a single side of an opaque web.

In the preferred embodiment of the present invention, the output of the light source 26 is controlled by a means for light sensing 30 that is mounted near the light detecting means 24, so that the light sensor "sees" approximately the same light as is "seen" by the light detecting means and can, accordingly, regulate the output of the light source to provide a consistent amount of light at the input of the light detecting means. When two cameras 24 are used as the light detecting means, it would be appropriate to place the light sensor 30 between the cameras. In a preferred embodiment of the present invention, the light sensor 30 would preferably be an illumination control assembly, Part No. 0100-0054, as is commercially available from FlowVision, Inc.

The output signal from the video cameras 24 or other light detecting means is transmitted to a light analyzing means 32 to observe variations in the detected light. One such light analyzing means would be an oscilloscope 32 that would visually display the light intensity signal transmitted by the light detecting means 24. Associated with the light analyzing means 32 is a means 34 for indicating that a variation beyond a threshold amount has been observed by the light analyzing means. In one embodiment of the invention, the indicating means 34 is an audio alarm that will sound to alert the operator of the unacceptable variation. Another possible indicating means 34 is a ink jet positioned towards the takeup roll 18 from the inspection stage 22 that will cause a visible mark to be made at the edge of the web 100 near the point of the contaminant. An even further indicating means 34 is a brake to automatically stop the web 100.

The device 10 described so far would operate to identify contaminant markings on a pristine web 100 of material, but the device would not be able to discriminate between contaminant marking and intentional printing made upon the web, which is the usual case encountered commercially. Therefore, a further feature of the device 10 enables it to operate on a web 100 of material imprinted with a monochrome series of markings, provided that certain limitations on the color of the monochrome markings are observed. In a monochrome marking, all light falling on the marking is absorbed except for a certain wavelength, which is reflected, resulting in the characteristic monochrome. If all light reflecting off of or passing through the web surface is passed through a filter 36 which absorbs all light except for that same wavelength reflected by the monochrome markings, then the monochrome markings will essentially blend into the background and they will be indistinguishable from the background.

There are two distinct manners of achieving this result. The first method is to condition all light received at the light detecting means 24 by placing the filter 36 at the iris or light input of the light detecting means. In a second method, the light allowed to be reflected off of or passed through the web 100 is conditioned by a monochrome filter 36 at or near the light source 26, so that the only light available to reflect off of or pass through the web surface already is of a monochrome nature. Of these, either will function, the conditioning just prior to the entry into the light detecting means being preferred, since it is much more reliable and is not subject to the interference of external unfiltered light.

There are, of course, some limitations to the colors that may be "masked" by this technique. As a first example, consider a black marking on an otherwise clear web background. By definition, "black" indicates that all light is absorbed by the marking surface and none is reflected. In order to make the background indistinguishable, the filter would have to absorb all light entering it, resulting in the reception of no light at the light detecting means 24 and obviating the effectiveness of the result. As a further example, a "white" marking would, by definition, reflect all light, absorbing none, and no filter 36 would be necessary. A "red" color, that is a color having a characteristic absorption wavelength in the "red" portion of the visible spectrum, is the preferred color from the experimentation conducted to date.

The interaction of the light analyzing means 32 and the indicating means 34 is an important aspect of the present invention. The output signal arriving at the light analyzing means 32 through standard electrical communication with the light detecting means 24 may be displayed visually, as in an oscilloscope, such as a Model 2225 commercially available from Tektronix Corporation of Beaverton, Oreg. The output signal may also be processed through a video processor unit such as the Model VP-2 video processor, available commercially from Flow Vision. The oscilloscope is mainly intended for verification of the proper alignment of the cameras 24 relative to the web, since an inconsistent alignment will result in reduced scanning sensitivity. For example, if the camera view is improperly aligned with either the web imprinting or the light source 26, the camera output will vary across the scanning image and detection of variations of at least threshold value will not be properly made.

When a defect is encountered on the web 100 as it passes the inspection stage 22 and is viewed by the cameras 24 or other light detecting means, one type of common defect observed is a pinhole in the web, which is observed as a positive spike 38, due to the increased light captured. A typical oscilloscope display illustrating such a spike is shown in FIG. 2. Therefore, the light analyzing means 32 is set to trigger the indicating means 34 when a positive light intensity above a threshold value is detected. Similarly, the presence of dark particles result in a negative spike 40, due to the decreased light captured, and the light analyzing means 32 should trigger the indicating means 34 when the light detected goes below a threshold value.

It will be appreciated that the sensitivity setting that results in spikes on the oscilloscope, either positive or negative, will need to be set according to web speed and size of the particle to be detected. More particularly, the faster the web speed past the inspection stage, the greater the sensitivity required to detect defects. For example, a defect large enough to be detected at a sensitivity of 400 (on a relative scale as described below) at a web speed of 400 feet/min. may require a sensitivity of 430 for inspection at 750 feet/min. When the Flow Vision unit described above is used, the most sensitive setting is described as a sensitivity of 500, such that readings of 500 to 1000 are referred to as positive spikes and readings from 0 to 100 are negative spikes. This relates to any slight deflection the baseline reading of the oscilloscope triggering the indicating means. A sensitivity of 0 or 1000, on the other hand, would relate to a full-scale deflection of the baseline signal without triggering the indicating means. The invention is also believed to be somewhat sensitive to web material and thickness, the preferred materials being nylon and polyethylene, and the preferred thickness being less than 5 mils.

Just as the present invention relates to a device for detecting contaminant particles on a surface of a monochrome web of material of a first color and imprinted with a second color different from the first color, the invention also relates to a method for detecting such contaminants, comprising the steps of:

(a) passing the monochrome web 100 from a feed roll 16 to a takeup roll 18 on a detection device 10, while the web moves past an inspection stage 22 between the feed roll and the takeup roll;

(b) collecting light from a light detecting means 24 by transversely scanning the surface of said web with said light detecting means as the web moves past the intermediate portion;

(c) analyzing for variations in the intensity of said detected light by use of a light analyzing means 32; and (d) causing observed variations in the detected light intensity beyond a threshold amount to trigger an indicating means 34.

This method operates with monochrome webs 100 that are transparent or translucent and the light collected in step (b) is passed through the web. The method also operates with opaque monochrome webs, where the light collected in step (b) is reflected off of the imprinted surface of the web.

The method also operates where the light collected in step (b) is passed through a filter immediately prior to collection in the light detection device, the filter being selected so that the first color of the web is indistinguishable from the second color of the imprinting after passage through the filter.

The method may be operated with a variety of indicating means, including an audio alarm, an ink jet to mark the edge of the web near the point of the defect, or a brake to stop the web.

While in accordance with the patent statutes, the best mode and preferred embodiment of the invention have been described, it is to be understood that the invention is not limited thereto, but rather is to be measured by the scope and spirit of the appended claims.

What is claimed is:

1. A device for detecting contaminant particles on a surface of a monochrome web of material of a first color having monochrome printing of a second color different from said first color, said device comprising:

a frame member with a means for mounting a feed roll of said printed web material and a means for mounting a takeup roll, said printed web material passing from said feed roll to said takeup roll;

a light source to direct a light beam onto the printed web;

an intermediate portion between said feed roll and said takeup roll, said intermediate portion having a light detecting means mounted thereupon for collecting light transversely from said printed web as said printed web passes past the intermediate portion, said light detecting means having a filter so that the light collected in the light detecting means passes through the filter before entering the light detecting means, the filter selected so that said first color is indistinguishable from said second color after passage through the filter;

a light analyzing means to determine that variation beyond a threshold amount has been observed by the light detecting means, said light analyzing means communicated to said light detecting means; and an indicating means to notify a human operator that a variation beyond a threshold amount has been observed by the light detecting means and determined by the light analyzing means, said indicating means communicated to said light analyzing means.

2. The device of claim 1 wherein the indicating means is an audio alarm.

3. The device of claim 1 wherein the indicating means is a ink jet.

4. The device of claim 1 wherein the indicating means is an automatic brake to stop the movement of the web.

5. The device of claim 1 wherein the intermediate portion has a light controlling means mounted thereon proximate to the light detecting means and communicated to said light source, to control the amount of light emitted from said light source.

6. The device of claim 1 wherein the light source is located on the same side of the web as the light detecting means and the light detected is reflected off of a first surface of said web.

7. The device of claim 1 wherein the light source is located on the opposite side of the web from the light detecting means and the light detected is passed through the web.

8. A method for detecting contaminant particles on a surface of a monochrome web of material of a first color and imprinted with a second color different from the first color, said method comprising the steps of:

(a) passing said printed web from a feed roll to a takeup roll on a detection device, said printed web moving past an intermediate portion of said detection device between said feed roll and said takeup roll;

(b) collecting light from a light source in a light detecting means by transversely scanning the surface of said printed web with the light detection means as the printed web moves past the intermediate portion, said collected light passing through a filter, said filter selected so that said first color is indistinguishable from said second color after passage through said filter, prior to collection in the light detecting means;

(c) analyzing for variations in the intensity of said collected light; and (d) causing observed variations in the collected light intensity beyond a threshold amount to trigger an indicating means.

9. The method of claim 8 wherein the monochrome web is transparent or translucent and the light collected in step (b) is passed through the web.

10. The method of claim 8 wherein the indicating means is an audio alarm.

11. The method of claim 8 wherein the indicating means is an ink jet.

12. The method of claim 8 wherein the indicating means is an automatic brake to stop the movement of the web.

13. The method of claim 8 wherein the monochrome web is opaque and the light collected in step (b) is reflected off of the imprinted surface of the web.

* * * * *